(12) United States Patent
Krivoi et al.

(10) Patent No.: US 6,501,266 B1
(45) Date of Patent: Dec. 31, 2002

(54) PROCEDURE AND DEVICE FOR DETECTING NONUNIFORMITIES IN THE WALL THICKNESS OF INACCESSIBLE METAL PIPES

(75) Inventors: Guennadi Krivoi, Berlin (DE); Martin Klinger, Malente (DE); Johann H. Hinken, Hildesheim (DE)

(73) Assignee: F.I.T. Messtechnik GmbH (DE)

( * ) Notice: Subject to any disclaimer, the term of this patent is extended or adjusted under 35 U.S.C. 154(b) by 0 days.

(21) Appl. No.: 09/674,174

(22) PCT Filed: Apr. 27, 1999

(86) PCT No.: PCT/EP99/02851
§ 371 (c)(1),
(2), (4) Date: Sep. 29, 2000

(87) PCT Pub. No.: WO99/56123
PCT Pub. Date: Nov. 4, 1999

(51) Int. Cl.[7] .............................................. G01N 27/82
(52) U.S. Cl. .................... 324/238; 324/229; 324/263
(58) Field of Search ................... 324/219, 229, 324/232, 238, 239, 240, 260, 263, 220, 221

(56) References Cited

U.S. PATENT DOCUMENTS

| | | | | |
|---|---|---|---|---|
| 4,048,558 A | | 9/1977 | Goodman | 324/57 |
| 4,608,534 A | * | 8/1986 | Cecco et al. | 324/238 |
| 4,947,132 A | * | 8/1990 | Charoy et al. | 324/699 |
| 4,982,158 A | * | 1/1991 | Nakata et al. | 324/263 |
| 5,864,229 A | * | 1/1999 | Lund | 324/240 |

FOREIGN PATENT DOCUMENTS

GB  2 143 331 A  2/1985 .................... 27/83

* cited by examiner

Primary Examiner—Edward Lefkowitz
Assistant Examiner—Subhash Zaveri
(74) Attorney, Agent, or Firm—Leydig, Voit & Mayer, Ltd.

(57) ABSTRACT

The invention concerns a testing procedure for detecting nonuniformities in the wall thickness of inaccessible metallic pipes in which electrical alternating currents of different frequencies are passed through the pipe and the magnetic fields generated by them are measured outside the pipe. The invention further concerns a device, particularly for carrying out the testing procedure, comprising a power source for passing an alternating current through the pipe, at least one magnetic field probe for measuring outside the pipe the magnetic field generated by the alternating current, and equipment for the evaluation which deduces the presence of a nonuniformity in wall thickness from the magnetic field signal of the magnetic field probe.

15 Claims, 5 Drawing Sheets

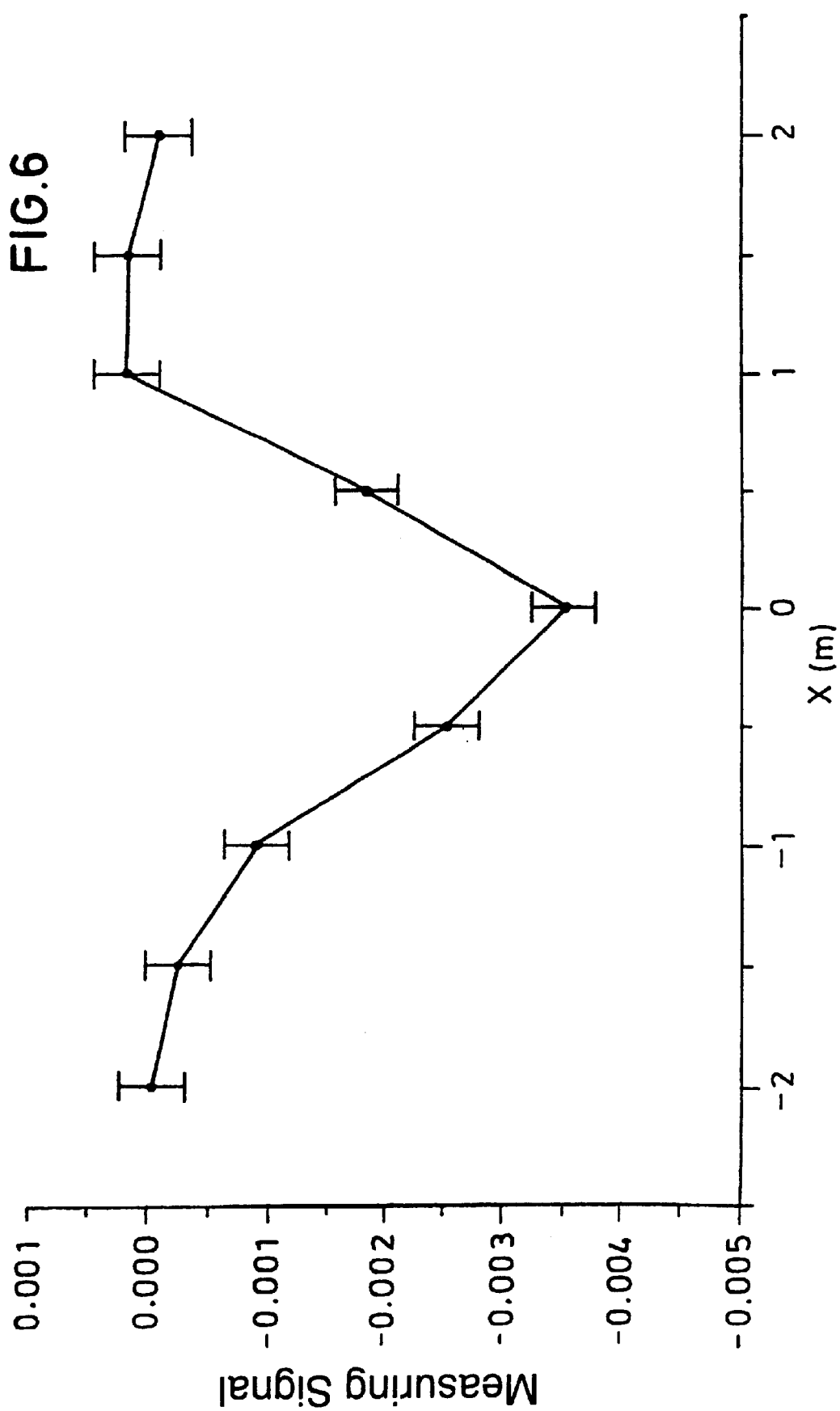

PROCEDURE AND DEVICE FOR DETECTING NONUNIFORMITIES IN THE WALL THICKNESS OF INACCESSIBLE METAL PIPES

FIELD OF THE INVENTION

The present invention concerns a procedure for detecting nonuniformities in the wall thickness of inaccessible metal pipes as well as a device particularly for carrying out the procedure.

BACKGROUND OF THE INVENTION

Nowadays pipes, and in particularly pipelines that are buried or not directly accessible for other reasons are tested with so-called pigs or rabbits. Conventional pigs are known from: Non-destructive Testing Handbook, Second Edition, Volume 10, Non-destructive Testing Overview, American Society for Non-destructive Testing, 1996, p. 252. Here an essential testing objective is that of measuring the current wall thickness as a function of peripheral angle and length coordinate. To this end the pig is equipped with different probes, for instance for ultrasonic tests, leakage flux tests and the mechanical probing or measuring of the inside diameter.

Among the disadvantages or limits in the use of such pigs one finds pipe bends with overly small bending radius, nonaxial end joints with an overly high difference angle between the axes, an overly small pipe inside diameter, excessive changes in diameter, the off-line evaluation and a considerable technical effort.

DE 4004170 A1 concerns a procedure and device for the monitoring of appearance and propagation of fractures or crevices in materials, parts, components, buildings or celestial bodies, particularly in areas with seismic risks or during rock movements in tunnel construction. However, this procedure only provides for a determination of electric field variations. An active measuring arrangement in which a current is passed through pipes is missing in this document.

DE 4105842 A1 concerns a procedure for locating couplings in burried ferromagnetic pipelines. Here the detection of seals or couplings is the prime consideration. The procedure provides for an artificial magnetization of the pipe element via a field winding in the pipe. The passage of a current is not disclosed.

DE 3623588 A1 concerns a procedure for locating electric lines that are not in the open. This procedure provides for connection of the feed cables to an electric audiofrequency generator while a searching probe serves as an electrical audiofrequency receiver. Here again no anomalies in pipes are detected by passing currents.

Finally a procedure is known from U.S. Pat. No. 4,048,558 where a current is passed through a metal pipe with different frequencies, and the impedance is monitored.

SUMMARY OF THE INVENTION

The invention is based on the objective of indicating a procedure and a device for detecting nonuniformities in the wall thickness of inaccessible metallic pipes wherein it is possible to recognize without making contact, and from a certain distance, whether the wall thickness of a pipe to be surveyed is nonuniform peripherally. Such nonuniformities can arise as a consequence of corrosion, for instance from the inside. Pipes deeply buried and obscured by other layers should in particular also be made accessible to testing.

This objective is attained according to the invention by a testing procedure according to claim 1 and by a device particularly for carrying out the testing procedure according to claim 13. The invention provides a nondestructive testing procedure as well as a corresponding device for recognizing without contact nonuniformities in the wall thickness of inaccessible metallic pipes. Such nonuniformities being primarily produced by corrosion, this procedure is particularly useful for an early detection of wall thickness reductions due to corrosion in pipelines. The procedure is based on the passage of electric currents of different frequencies through the pipe. The depth of penetration of the current into the wall being a function of frequency, a shift in the center of gravity of the currents and thus in the magnetic field strength measured at the measuring distance from the pipe will result when damage is present. The device is transportable.

It is preferred that the alternating currents comprise two different frequency components. It is preferred that the magnetic fields are measured at the same place. It is further preferred that the two frequency components are generated by currents having the same amplitudes, and that the ratio of the magnetic field components is evaluated. It is further preferred to first calculate the ratios of magnetic field to current at the individual frequencies, then calculate their ratio and subsequently evaluate it. Then it is preferred that the currents having different frequencies are simultaneously passed through the pipe. It is further preferred that the return current is passed through a line which runs preferably parallel at a certain distance from the pipe being surveyed. Preferably, furthermore, a magnetic field probe is provided which measures the peripheral component of the magnetic field. Alternatively, a magnetic field probe is provided which measures the magnetic field component tangential to ground level. Alternatively, a magnetic field probe is finally provided which measures the magnetic field component normal to ground level.

Finally, preferably at least two probes are provided with which measurements are made simultaneously in order to be able to locate the pipe. The current having the lowest frequency can in the limiting case essentially be a direct current.

In the device particularly for carrying out the procedure, preferably current measuring equipment is provided which measures the current flowing through the pipe. It is furthermore preferred that the equipment for evaluation accepts as well the signal for the current supplied by the current measuring equipment, and evaluates the ratio of magnetic field signal to current signal.

Further advantages, features and applications of the present invention will result from the following description of preferred embodiments in connection with the drawing.

BRIEF DESCRIPTION OF THE DRAWINGS

FIG. 6 shows the measuring signal arising from the artificial defect and in its neighborhood.

DETAILED DESCRIPTION OF THE INVENTION

Figure 1A:
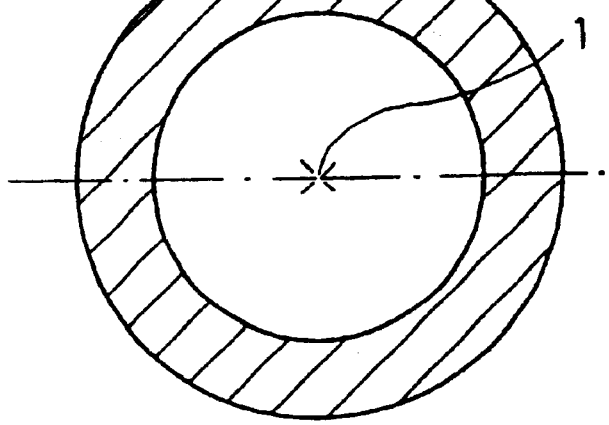
FIG. 1a shows the current distribution at low frequency for a pipe cross section without defect.
Figure 1B:
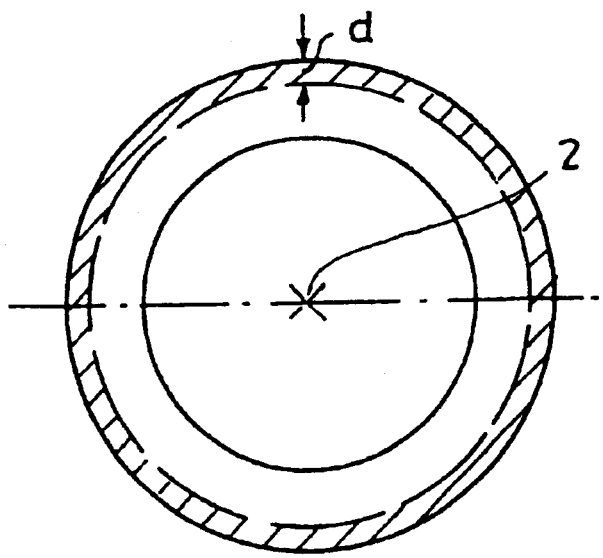
FIG. 1b shows the current distribution at high frequency for a pipe cross section without defect.

FIG. 1a shows the current distribution at low frequency in the instance of a pipe cross section without defect. The imposed current flows in the pipe's longitudinal direction, i.e., normal to the paper plane. At low frequencies, i.e., under conditions where the skin penetration is approximately equal to or larger than the wall thickness, the wall is fully penetrated by the current. FIG. 1b shows the same situation when applying a current of high frequency. At high frequencies the current is displaced toward the outer surface and merely flows within a depth of penetration d. Because of the symmetry of the arrangement, the centers of gravity of the currents 1 and 2 coincide. The measuring points 3 and 4 coincide. For the same current density, the same magnetic field strength will then be measured at measuring point 3 or 4.

Figure 2A:
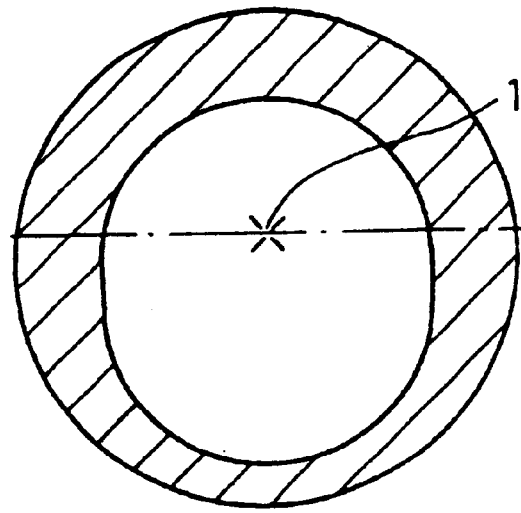
FIG. 2a shows the current distribution at low frequency in the instance of a pipe cross section with defect, viz., a wall thinning at the bottom inside.
Figure 2B:
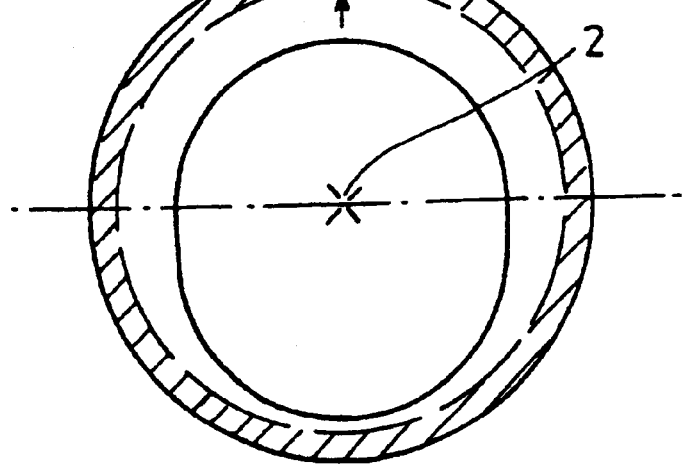
FIG. 2b shows the current distribution at high frequency in the instance of a pipe cross section with defect, viz., a wall thinning at the bottom inside.

FIGS. 2a and 2b show pipe cross sections with a defect, that is, a thinning of wall thickness on the inside. At a sufficiently low frequency the current will uniformly penetrate the entire cross-sectional area of the wall that is available. However, because of the asymmetric current distribution, here the cross section of the current has shifted upward according to FIG. 2a when seen from from the center of the outer circle. FIG. 2b shows the current distribution at a sufficiently high frequency. This is unchanged relative to the distribution without defect. The center of gravity of the current coincides with the center of the outer circle. Relative to the measuring points 3 and 4, the distance to the center of gravity of the current is smaller at low frequencies, and larger at high frequencies. For identical currents, the magnetic field generated at measuring point 3 at low frequencies will then be higher than that generated at measuring point 4 at high frequencies. In the procedure according to the invention, on principle alternating currents having different frequencies but the same amplitude are passed longitudinally through the pipe to be surveyed. The magnetic field strength is measured for both frequencies at the same place above the pipe. A different field strength indicates a nonuniformity in wall thickness. The procedure needs no access to the interior of the pipe to be surveyed. Electrical currents having different frequencies are passed along a survey section through the pipe to be surveyed.

Figure 3:
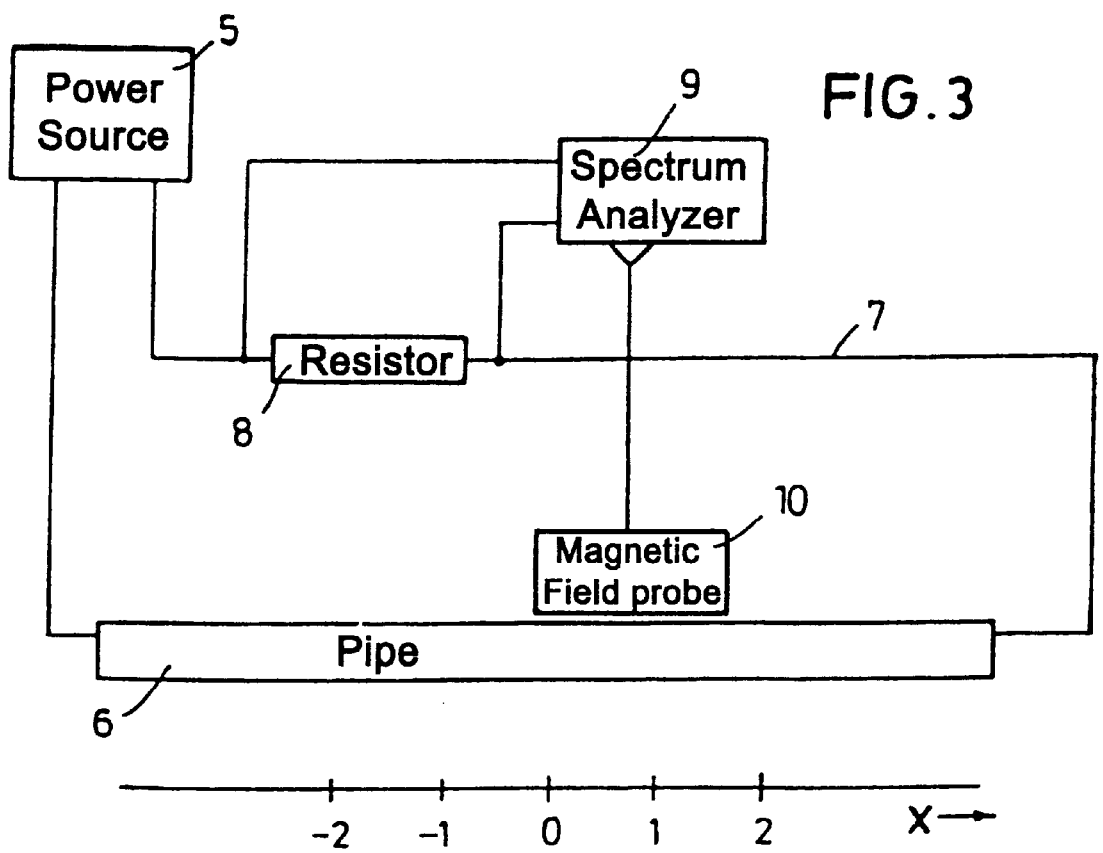
FIG. 3 shows the schematic composition of the device for carrying out the testing procedure.

FIG. 3 shows the basic arrangement of the measuring equipment. A power source 5 generates the measuring current. This is passed through the pipe 6 to be surveyed, and returned via a return line 7 found a few meters away from the object to be surveyed. The return line 7 is preferably arranged in parallel to the pipe 6. The current circuit contains a measuring resistor 8 the voltage drop across which is a measure of the measuring current. This voltage drop is fed to one channel of a spectrum analyzer 9 serving as equipment for the evaluation. The second channel of spectrum analyzer 9 receives the measuring signal from a magnetic field probe 10. The magnetic field probe 10 is arranged so that it can be shifted in the x-direction, that is, in the pipe's longitudinal direction.

In an embodiment modifying the basic measuring procedure, the two currents of different frequency are simultaneously passed through the object being surveyed.

Figure 4:
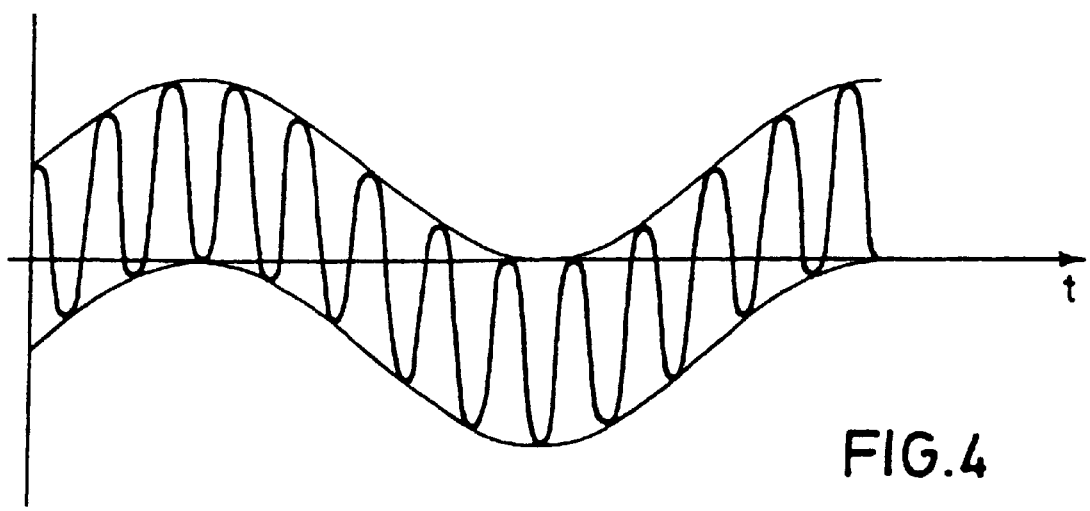
FIG. 4 shows the current signal of the power source as a function of time.

FIG. 4 shows the current signal as a function of time (not to scale). The frequencies $f_1=10$ Hz and $f_2=1$ kHz.

Figure 5A:
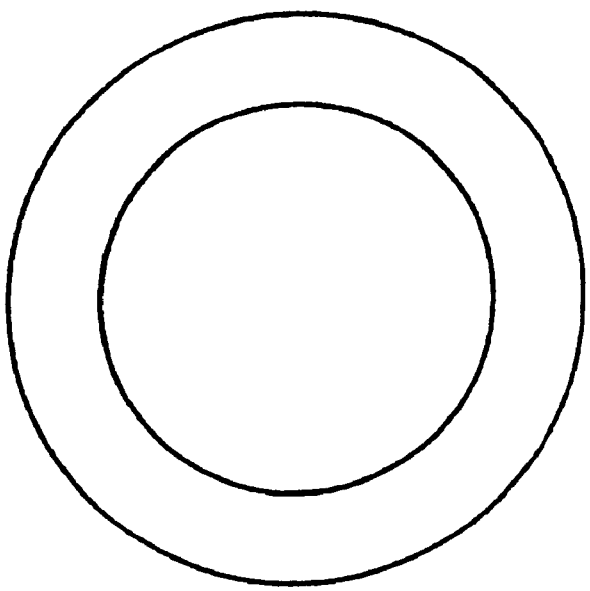
FIG. 5a shows a pipe cross section without defect.
Figure 5B:
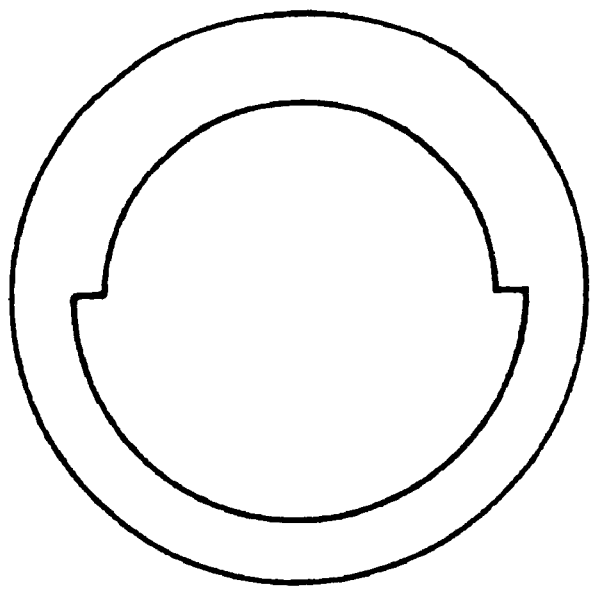
FIG. 5b shows a pipe cross section with an artificial defect.

FIG. 5 shows the cross section of a pipe 7 m long, with FIG. 5a showing the pipe cross section without defect and FIG. 5b the pipe cross section with an artificial defect stretching from x=−0.5 m to x=+0.5 m.

In a further embodiment further modifying the basic measuring procedure described above, not the ratio of the magnetic field strengths at frequencies $f_1$ and $f_2$ is plotted as the result of the measurements for identical currents but the ratio, reduced by one, of the corresponding ratios of magnetic field to current. This accounts for a nonuniformity of the current amplitudes at $f_1$ and $f_2$. This value is plotted in FIG. 6 against the probe position x. The probe is located outside the pipe at 55 cm here. The current amplitudes are 6.5 A each. FIG. 6 distinctly shows that the artificial defect is present. The measuring signal is distinctly larger than the error range entered for each measuring value in FIG. 6 as an error bar.

What is claimed is:

1. Test procedure for detecting nonuniformities in the wall thickness of inaccessible metallic pipes, characterized in that electrical alternating currents having at least two different frequency components having approximately the same amplitude are simultaneously passed through the pipe, a return current being passed through a return line, and the magnetic fields generated by the alternating currents are measured at a certain measuring distance outside the pipe.

2. Procedure according to claim 1, characterized in that the alternating currents comprise two different frequency components.

3. Procedure according to claim 2, characterized in that the magnetic fields are measured at the same place.

4. Procedure according to claim 2, characterized in that the two frequency components have the same amplitude and that the ratio of the magnetic field components is evaluated.

5. Procedure according to claim 4, characterized in that first the ratios of magnetic field to current are calculated at the individual frequencies, and then their ratio is calculated and subsequently evaluated.

6. Procedure according to claim 1, characterized in that the return line runs parallel along the pipe to be surveyed.

7. Procedure according to claim 1, characterized in that a magnetic field probe is provided which measures the peripheral component of the magnetic field.

8. Procedure according to claim 1, characterized in that a magnetic field probe is provided which measures the magnetic field component tangential to ground level.

9. Procedure according to claim 1, characterized in that a magnetic field probe is provided which measures the magnetic field component normal to ground level.

10. Procedure according to claim 1, characterized in that measurements are made with at least two probes simultaneously in order to be able to determine the position of the pipe.

11. Procedure according to claim 1, characterized in that the current at the lowest frequency is essentially a direct current.

12. Device, for detecting nonuniformities in the wall thickness of inaccessible pipes comprising;

a power source (5) to simultaneously pass alternating currents of different frequencies through the pipe (6), at least one magnetic field probe (10) arranged at a measuring distance from the pipe (6) to measure outside the pipe (6) the magnetic fields generated by the alternating currents, and equipment for evaluation (9) to deduce the presence of a nonuniformity it wall thickness from the magnetic field signal of the magnetic field probe (10).

13. Device according to claim 12, characterized in that current measuring equipment is provided for measuring the current flowing through the pipe.

14. Device according to claim 13, characterized in that the equipment for evaluation (9) accepts as well the signal for the current supplied by the current measuring equipment, and evaluates the ratio of magnetic field signal to current signal.

15. Procedure according to claim 3 characterized in that the two frequency components are generated by currents being the same amplitude and that the ratio of the magnetic field components is evaluated.

* * * * *

UNITED STATES PATENT AND TRADEMARK OFFICE
CERTIFICATE OF CORRECTION

PATENT NO. : 6,501,266 B1
DATED : December 31, 2002
INVENTOR(S) : Krivoi et al.

It is certified that error appears in the above-identified patent and that said Letters Patent is hereby corrected as shown below:

Title page,
Item [86], "§ 371 (c)(1), (2), (4) Date:" change "Sep. 29, 2000" to -- Nov. 29, 2000 --.

Column 5,
Line 2, change "it" to -- in --.

Signed and Sealed this

Twenty-ninth Day of April, 2003

JAMES E. ROGAN
*Director of the United States Patent and Trademark Office*